United States Patent [19]

Crow

[11] 4,437,464
[45] Mar. 20, 1984

[54] ELECTROSURGICAL GENERATOR SAFETY APPARATUS

[75] Inventor: James J. Crow, Englewood, Colo.

[73] Assignee: C.R. Bard, Inc., Murray Hill, N.J.

[21] Appl. No.: 319,423

[22] Filed: Nov. 9, 1981

[51] Int. Cl.³ .............................................. A61B 17/39
[52] U.S. Cl. ........................... 128/303.14; 128/303.17; 128/908
[58] Field of Search ...................... 128/303.13, 303.14, 128/303.17, 908

[56] References Cited

U.S. PATENT DOCUMENTS

| | | | |
|---|---|---|---|
| 3,478,744 | 11/1969 | Leiter | 128/303.14 |
| 3,683,923 | 8/1972 | Anderson | 128/303.14 |
| 3,946,738 | 3/1976 | Newton et al. | 128/303.14 |
| 4,094,320 | 6/1978 | Newton et al. | 128/303.14 |

FOREIGN PATENT DOCUMENTS 1541501  3/1979  United Kingdom ................ 128/908

*Primary Examiner*—Lee S. Cohen
*Attorney, Agent, or Firm*—Wolf, Greenfield & Sacks

[57] ABSTRACT

Leakage cancelling apparatus suitable for use in electrosurgery apparatus to prevent electrical burns is disclosed. The apparatus comprises a transformer which is connected in the electrical circuit between the electrosurgical source and the patient. The transformer has a primary winding connected in series with the active surgical electrode and a secondary winding connected in series with the return path to the electrosurgical generator. The connections to the windings are polarized so that during normal operation the magnetic fields in the transformer core generated by current flow are almost completely cancelled. Consequently, the transformer windings present very small impedances in series with the electrosurgical circuit. If a break occurs in the return lead of the electrosurgical circuit and the patient becomes ungrounded, a condition which would normally result in a high risk of a burn, the currents in the primary and secondary windings of the transformer become unequal, the magnetic fields in the transformer core do not cancel and the transformer windings present a significant impedance to the flow of electrosurgical current which reduces the occurence of electrosurgical burns. In addition, the uncanceled inductance presented by the transformer windings during a break situation may be chosen to resonate with the leakage capacitance of the electrosurgical circuit, further reducing the current flow and preventing burns.

10 Claims, 4 Drawing Figures

ELECTROSURGICAL GENERATOR SAFETY APPARATUS

FIELD OF THE INVENTION

This invention relates to safety circuits and more particularly to leakage cancelling circuits suitable for use with electrosurgery apparatus.

BACKGROUND OF THE INVENTION

Electrosurgery is a well-known and widely used technique for performing cutting and coagulation surgical operations. In order to perform an electrosurgery operation, the patient is connected to a electrical energy generator which produces high-frequency energy, generally in the frequency range of 100 kilohertz to 1 megahertz. The high-frequency energy is supplied to the patient at the operating area by means of an "active" electrode which has a small contact area with the patient. The high-frequency electrosurgical source is capable of producing a significant amount of current at a relatively high voltages and the high current density caused by the small contact area of the active electrode causes a localized cutting or coagulating action. The current, after flowing through the operation point, is returned to the high-frequency generator via an indifferent electrode or return plate. The current return point typically has a large contact area with the patient so that the density of current flowing from the patient to the plate is low at all contact points. The low current density prevents electrical burns from occurring at the point where the indifferent electrode contacts the patient.

Most prior art electrosurgery apparatus suffers from a common disadvantage in that the patient can suffer severe electrical burns if the electrosurgical current leaves the patient's body via a route other than the indifferent electrode. Surgical burns can be caused by secondary grounds which establish an alternative current path. If the area of the contact point at which the current leaves the patient's body is small, a burn can result. Secondary ground paths can occur over monitoring electrodes connected between the patient and grounded electrical monitoring equipment; additional ground paths can occur between the patient and a grounded support or operating table or between the patient and the surgeon.

Unfortunately, such burns can be quite severe because the patient is often unconscious during the surgical operation and therefore does not react. Consequently, burning can occur over a considerable period of time during which surgery is taking place.

In order to attempt to eliminate the problem of burns caused by alternate grounding paths, an electrosurgical generator that has an isolating output transformer is used. In this type of generator, the electrical power generated by the output stage of the generator is coupled to the active and indifferent electrodes by means of the secondary winding of a transformer which is not connected to the primary winding and is not grounded. Unfortunately, because of stray or leakage capacitance between the transformer windings and between the secondary winding and ground, the electrical isolation is far from perfect and severe patient burns can result if the return cable connecting the indifferent electrode plate to the electrosurgical source is broken or the patient moves out of contact with the indifferent electrode plate.

It is, therefore, an object of this invention to provide a cancelling circuit which cancels out leakage produced by improper grounding of the electrosurgical unit and prevents electrical patient burns.

It is a further object of this invention to provide a leakage cancelling circuit suitable for use with electrosurgery apparatus to prevent electrical burns.

It is another object of this invention to provide a leakage cancelling circuit capable of reducing the current flow through the patient at secondary ground points when an indifferent electrode connection to the patient is broken either because of inadequate patient contact to the indifferent electrode or because of a break in the line connecting the indifferent electrode to the electrosurgical generator.

SUMMARY OF THE INVENTION

The foregoing problems are solved and the foregoing objects are achieved in one illustrative embodiment of the invention in which a leakage cancelling transformer having closely-coupled primary and secondary windings is connected in the electrical circuit between the electrosurgical generator and the patient. The primary winding is connected electrically in series with the active lead and the secondary winding is connected electrically in series with the return lead. The windings are polarized and connected so that the magnetic fields in the transformer core generated by electrosurgical current flowing in the windings tend to cancel. Therefore, during normal operation when the electrosurgical current running through the active lead is approximately equal to the electrosurgical current running through the return lead, the magnetic field within the transformer core is very small, causing the impedance of the transformer windings to be very low. When, however, the current flow in the primary and secondary windings becomes imbalanced because of an abnormal condition, the magnetic field within the transformer core is not completely cancelled, resulting in a substantial winding impedance being placed electrically in series between the patient and the electrosurgical generator. This impedance significantly reduces the electrosurgical current flowing to the patient and prevents severe patient burns.

In particular, the primary and secondary windings on the transformer core are closely matched in number of turns and physical placement to result in a nearly complete cancellation of the magnetic field within the transformer core when the system is operating in the normal mode in which the currents in the active lead and return lead are balanced.

In accordance with a further principle of the invention, the placement and number of windings on the transformer is chosen so that the uncanceled winding inductance is resonant with leakage capacitance at the operating frequency of the electrosurgical source. Under these conditions, the impedance of the resonant circuit can reach high values which are eliminated primarily by the "Q" of the resonant circuit and the patient impedance. Consequently, the potential for severe burns is substantially eliminated.

In accordance with yet further principles of the invention, the leakage cancelling transformer may be provided with multiple primaries windings to allow the alternative use of several active electrodes.

Still further in accordance with the principles of the invention, the leakage cancelling transformer may be installed at any physical location in the active and return leads between the patient and the electrode in order to achieve cancellation of various leakage capacitances.

DETAILED DESCRIPTION

Figure 1:
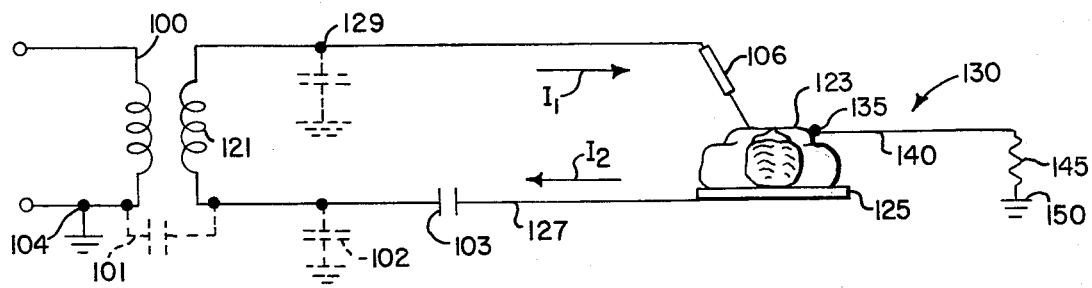
FIG. 1 of the drawing shows prior art electrosurgical apparatus in schematic form.

FIG. 1 of the drawing shows a prior art electrosurgery unit which has an electrically isolated output circuit. For purposes of clarity only the output transformer of the electrosurgery unit is shown. The remaining portions of the generator and its operations are well-known to those skilled in the art.

The electrosurgery apparatus produces a high-frequency signal in the primary 100 of the output transformer which, in turn, produces a high-frequency, high-voltage signal in secondary 121 of the output transformer. The electrosurgical power produced by the output transformer of the electrosurgery apparatus is provided, via lead 129, to active electrode 106 for performing electrosurgical operations on patient 123.

During an electrosurgical operation, the patient lies on, or is attached to, a return or indifferent electrode 125 and the current, I1, which flows through the active electrode 106 returns (I2) to the generator via return electrode 125 and lead 127 to the secondary winding of the output transformer. Electrosurgical operations, such as cutting or coagulation, can be performed by active electrode 106 because its contact area with patient 123 is small and therefore the local current density is high, producing heating and other effects which are well-known to the art.

Because the area of the indifferent electrode 125 is large the local current density is small and therefore no electrosurgical effects occur at the point where the current exits from the patient's body.

Normally, such a prior art system is designed so that the secondary winding 121 of the output transformer is electrically "isolated" or not connected to electrical ground. Electrical isolation is usually considered desirable for patient safety during electrosurgical operations. Theoretically, with perfect isolation, if a break 103 occurs in the return cable 127, current flow through the electrosurgical circuit would stop since there is not complete circuit between the patient and secondary 121 of the output transformer. Unfortunately, in practical surgical units, the theory goal is not realized because there are significant leakage capacitances between the active and the return cables (shown schematically as capacitors 115 and 102, respectively). In addition, there is generally a significant interwinding capacitance between the primary and secondary windings of the output transformer (shown schematically as capacitor 101).

Due to the leakage capacitance, a significant burn potential results if a break 103 should occur in the return cable because current entering the patient's body via active electrode 106 may return to the electrosurgical generator via alternate paths. These are shown schematically in FIG. 1 as circuit 130. An alternate path may result where the patient touches a grounded operating table or where monitoring electrodes connected to grounded electrical equipment are attached to the patient or through the surgeon himself. When an alternate ground path occurs, for example, at point 135, current may flow via lead 129, the active electrode 106, point 135 and the alternate grounding path (shown schematically as lead 140, resistor 145 and ground 150). Current running into the alternate path may then return, via leakage capacitance 102 to secondary 121 of the electrosurgical transformer or, since in most electrosurgical generators, the primary is grounded (at 104) through ground 104 and the interwinding capacitance 101 to the secondary winding.

Alternatively, a burn can be caused by a break in the active lead. In this case, current flows through the external circuit 130 into the patient and returns to the generator throught the normal return circuit.

If current flow over such a secondary path occurs, an electrical burn may occur at point 135 if the patient contact with the alternate path is small in area. Unfortunately, the patient may be under anaesthetic during the electrosurgical operation and may not react to the burning. In addition, since the patient is often covered during an electrosurgical operation the burn can go unnoticed and can become quite severe.

Figure 2:
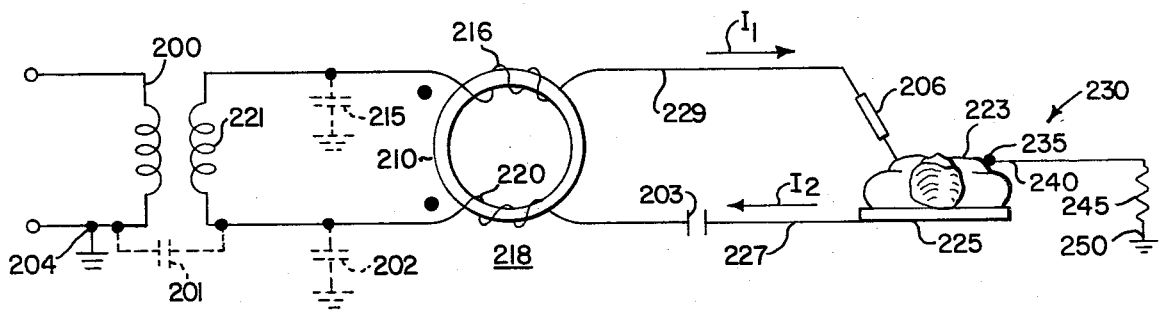
FIG. 2 of the drawing shows an electrosurgical apparatus with an illustrative leakage cancelling transformer installed electrically in series between the electrosurgical generator and patient.

FIG. 2 of the drawing shows an illustrative embodiment of the invention in which leakage cancelling transformer 218 has been inserted into the electrosurgical circuit. The transformer consists of core 210, primary winding 216 and secondary winding 220. During normal operation, electrosurgical current flows via primary winding 216 and lead 229 to active electrode 206. Current returns to the generator by way of indifferent electrode 225, lead 227, secondary winding 220 to secondary 221 of the electrosurgical output transformer.

Figure 3:
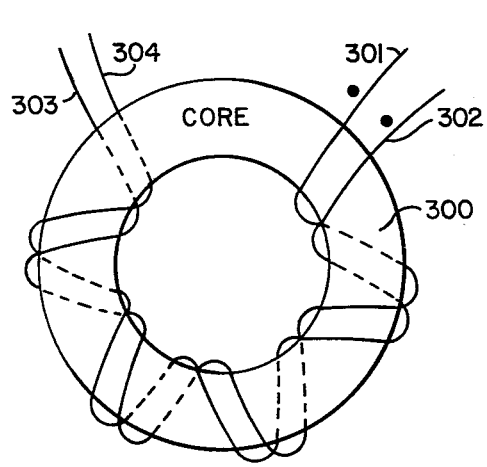
FIG. 3 of the drawing shows an illustration of the physical construction of a leakage cancelling transformer in accordance with the principles of the invention.

In FIG. 2, transformer 218 is shown schematically for purposes of clarity. Although the primary and secondary windings are shown separated in FIG. 2, they are actually closely matched in number of turns and physical placement as shown in FIG. 3. In FIG. 3, for example, the primary winding may be winding 301–303 and the secondary winding may be winding 302–304 both of which are wound around a toroidal core 300.

The windings are connected in the electrosurgical circuit, as shown in FIG. 2, so that the active current, I1, flows through primary winding 216 in the opposite direction in which the return current, I2, flows through secondary winding 220. Due to the closely-matched windings and the opposite direction of current flow, there is almost complete cancellation of the magnetic field within transformer core 210.

Normally, the electrical impedance of a transformer winding at a specified operating frequency is dependent on the inductance of the winding which, in turn, is related to the strength of the magnetic field present in the transformer core. For example, in a typical illustrative transformer built in accordance with the principles of the invention, the inductance of one winding of the transformer (either primary or secondary) is approximately 3 millihenries when the other winding is open-circuited. However, when the windings are connected, as shown in FIG. 2, so that equal currents flow in opposite directions in the windings, the cancellation of the magnetic field in the transformer core causes the inductance of each winding to drop to approximately 3 microhenries or approximately 1/1000 of the uncancelled inductance. Accordingly, when the circuit is connected, as shown in FIG. 2, and equal currents flow in primary 216 and secondary 220 of the cancellation transformer, the impedance presented by the transformer windings is relatively small compared to the impedance seen by the active electrode through the patient. Specifically, in an illustrative transformer operating at an electrosurgery frequency of 500 kilohertz, the 3 microhenry inductance produces a total impedance of approximately 9 ohms. The patient impedance is approximately 200 ohms at this frequency. Because the electrosurgical power is proportional to the square of the current, the power lost in the transformer windings is less than 5% during normal operating conditions.

However, when a break 203 occurs in the return path and a leakage path is present, current will flow through lead 229, active electrode 206, through the patient 223 and out the alternate ground point 235 through ground circuit 230 comprised of lead 240 and resistor 245 to ground 250. Current will then flow either through leakage capacitance 202 or interwinding capacitance 201 as previously described. The result is that current flow through secondary 220 of the leakage cancelling transformer is reduced substantially to zero.

In this case, because there is no current returning through winding 220, there is no cancellation of the magnetic field within core 210 and primary winding 216 exhibits its entire normal impedance (illustratively 3 millihenries). At 500 kilohertz, the impedance of 3 millihenries is approximately 9000 ohms which is about 50 times the 200 ohm patient impedance. Thus, the current flowing through the patient is substantially reduced, thereby reducing the risk of patient burn.

In addition, the leakage current flowing through the patient may be even further reduced by choosing the value of the uncancelled transformer winding inductance so that it becomes parallel resonant with an appropriate leakage capacitance. In the case of a break in the return lead, the uncancelled winding inductance of winding 216 should be resonant with the active lead capacitance, denoted by capacitor 215. Under these circumstances the impedance of the resonant circuit can become very high, limited primarily by the "Q" of the resonant circuit and the 200 ohm patient impedance. Since the leakage capacitance (schematically represented as capacitor 215) is relatively fixed for each electrosurgical unit, it is possible to obtain a circuit which approaches resonance during a return cable break or improper ground condition. In particular, the capacitance and the uncancelled winding inductance can be chosen to resonate at the electrosurgical operating frequency.

In addition, the illustrative transformer can cancel leakage currents caused by an improper connection to the active electrosurgical lead (often caused by a break in the active lead or when the active lead is held away from the patient and the electrosurgical generator is turned on). Under these circumstances, the uncancelled winding inductance of winding 220 can be chosen to resonate at the electrosurgical operating frequency with the return lead leakage capaitance (schematically represented as capacitor 202). Since the return lead leakage capacitance is usually approximately equal to the active lead leakage capacitance in most electrosurgical units, the illustrative transformer windings will be resonant with both leakage capacitances and thus cancel leakage currents in both the return and active leads.

In the illustrative embodiment, shown in FIG. 3, the leakage cancelling transformer is composed of a powdered-iron core 300 which may illustratively be a model 400T750-3C8 manufactured by Ferroxcube, Inc., 5083 King's Highway, Saugerties, N.Y. 12477. Windings 301 and 302 are each composed of 22 gauge wire having 22 turns around the transformer core in close physical proximity as shown in FIG. 3.

The leakage cancelling transformer is effective when it is inserted anywhere into the active and return leads between the electrosurgical generator and the patient. For example, the transformer may be physically installed next to the secondary of the electrosurgical output transformer to cancel the transformer interwinding capacitance. The leakage cancelling transformer may be also placed directly behind the electrosurgical generator front panel to cancel the transformer interwinding capacity, lead capacity and any leakage capacity in auxiliary circuits, such as hand control switches or patient plate switches. The leakage cancelling transformer can also be placed in a location that is physically remote from the generator, for example in a box located on the operating table. This characteristic allows for convenient leakage cancelling in European operating rooms in which the electrosurgical generator is often located outside the operating room.

Figure 4:
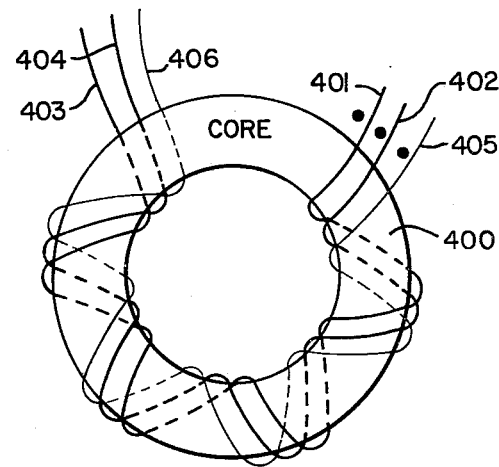
FIG. 4 of the drawing shows a multiple winding leakage cancelling transformer for use with multiple active electrodes.

Furthermore, in accordance with the invention, the leakage cancelling transformer may be used with electrosurgical units having several active electrodes such as monopolar electrodes controlled by foot switches and hand switches. In this case, as shown in FIG. 4, another primary winding 405–406 may simply be added to the normal primary and secondary windings 401–403 and 402–404 respectively) around transformer core 400. The active electrodes are connected to the two primary windings and the secondary winding is connected to the return electrode as shown in FIG. 2.

Although one illustrative embodiment has been illustrated herein, other modifications within the spirit and scope of the invention will become apparent to those skilled in the art. For example, the details of the transformer construction may be varied within the principles of this invention—other shaped cores and winding configurations may be used.

What is claimed is:

1. In an electrosurgical system having an electrosurgical generator for providing electrosurgical power at an operating frequency, an active electrode for applying said electrosurgical power to a patient, active electrical circuit means for connecting in a first electrical circuit said active electrode and said generator for supplying current from said generator to said active electrode and return electrical circuit means for returning said current in a second electrical circuit from said patient to said generator, the improvement comprising, safety apparatus for preventing patient burns, comprising, means responsive to the current flowing in said first circuit and responsive to the current flowing in said second circuit, for inserting an electrical impedance in series with said first circuit and said second circuit when said current flowing in said first circuit is not substantially equal to the current flowing in said second circuit, said impedance having a magnitude sufficient to reduce the current flowing in said first circuit and said second circuit to a value low enough to prevent patient burns.

2. The improvement according to claim 1 wherein said inserting means comprises a transformer having a core, a primary winding connected electrically in series with said first circuit, and a secondary winding connected electrically in series with said second system.

3. The improvement according to claim 2 wherein the open-circuit inductance of said primary winding and said secondary winding is resonant with leakage capacity in said electrosurgical system at said operating frequency.

4. The improvement according to claim 2 wherein said electrosurgical system has at least one additional active electrode and electrical circuit means for connecting said additional electrode in a third electrical circuit between said generator and said patient and said transformer has at least one additional primary winding connected in said third circuit.

5. In an electrosurgical system having an electrosurgical generator for providing electrosurgical power at an operating frequency, an active electrode for applying said electrosurgical power to a patient, active electrical circuit means for connecting in a first electrical circuit said active electrode and said generator and return electrical circuit means for returning current in a second electrical circuit from said patient to said generator, the improvement comprising, a transformer having a core, a primary winding connected electrically in series with said first circuit, and a secondary winding connected electrically in series with said second circuit, said primary and secondary windings being physically located on said core and being connected so that current passing through them generates opposing magnetic fields in said core, which fields substantially cancel, and wherein the open-circuit inductance of said primary winding and said secondary winding is resonant with leakage capacity in said electrosurgical system at said operating frequency.

6. The improvement according to claim 5 wherein said electrosurgical system has at least one additional active electrode and electrical circuit means for connecting said additional electrode in a third electrical circuit between said generator and said patient and said transformer has at least one additional primary winding connected in said third circuit.

7. An electrosurgical system comprising
   an electrosurgical generator for providing electrosurgical power at an operating frequency,
   an active electrode for applying said electrosurgical power to a patient,
   active electrical circuit means for connecting in a first electrical circuit said active electrode and said generator for supplying current from said generator to said active electrode,
   a return electrode for collecting current applied to a patient,
   return electrical circuit means for returning in a second electrical circuit said collected current to said generator,
   means responsive to the current flowing in said first circuit and responsive to the current flowing in said second circuit, for inserting an electrical impedance in series with said first circuit and said second circuit when said current flowing in said first circuit is not substantially equal to the current flowing in said second circuit, said impedance having a magnitude sufficient to reduce current flowing in said first circuit and said second circuit to a value low enough to prevent patient burns.

8. An electrosurgical system according to claim 7 wherein said inserting means comprises a transformer having a core, a primary winding connected electrically in series with said first circuit, and a secondary winding connected electrically in series with said second circuit.

9. An electrosurgical system according to claim 8 wherein the open-circuit inductance of said primary winding and said secondary winding is resonant with leakage capacity in said electrosurgical system at said operating frequency.

10. An electrosurgical system according to claim 9 wherein said electrosurgical system has at least one additional active electrode and electrical circuit means for connecting said additional electrode in a third electrical circuit between said generator and said patient and said transformer has at least one additional primary winding connected in said third circuit.

* * * * *